(12) United States Patent
Schraga

(10) Patent No.: US 8,034,069 B2
(45) Date of Patent: *Oct. 11, 2011

(54) SINGLE USE LANCET ASSEMBLY

(76) Inventor: Steven Schraga, Surfside, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/786,112

(22) Filed: May 24, 2010

(65) Prior Publication Data

US 2010/0305598 A1  Dec. 2, 2010

Related U.S. Application Data

(63) Continuation of application No. 10/894,865, filed on Jul. 20, 2004, now abandoned, which is a continuation-in-part of application No. 09/903,877, filed on Jul. 10, 2001, now Pat. No. 6,764,496, which is a continuation-in-part of application No. 09/432,351, filed on Nov. 2, 1999, now Pat. No. 6,258,112.

(51) Int. Cl.
*A61B 17/34* (2006.01)
*A61B 5/151* (2006.01)

(52) U.S. Cl. ..................................................... 606/182

(58) Field of Classification Search ............... 606/167, 606/181–183, 170, 184, 185; 600/583
See application file for complete search history.

(56) References Cited

U.S. PATENT DOCUMENTS

| 55,775 | A | 6/1866 | Klee |
|---|---|---|---|
| 2,711,738 | A | 6/1955 | Kelly et al. |
| 3,358,689 | A | 12/1967 | Higgins |
| 3,483,810 | A | 12/1969 | Peters et al. |
| 3,760,809 | A | 9/1973 | Campbell, Jr. |
| 3,906,626 | A | 9/1975 | Riuli |
| 4,139,011 | A | 2/1979 | Benoit et al. |
| 4,373,526 | A | 2/1983 | Kling |
| 4,414,975 | A | 11/1983 | Ryder et al. |
| 4,445,896 | A | 5/1984 | Gianturco |
| 4,449,529 | A * | 5/1984 | Burns et al. ................... 606/182 |
| 4,469,110 | A | 9/1984 | Slama |
| 4,517,978 | A | 5/1985 | Levin et al. |
| 4,535,769 | A | 8/1985 | Burns |
| 4,539,988 | A | 9/1985 | Shirley et al. |
| 4,573,976 | A | 3/1986 | Sampson et al. |
| 4,610,620 | A | 9/1986 | Gray |
| 4,655,750 | A | 4/1987 | Vaillancourt |
| 4,665,959 | A | 5/1987 | Takagi |

(Continued)

FOREIGN PATENT DOCUMENTS

CA  2 261 852 A1  8/1999

(Continued)

*Primary Examiner* — Kathleen Sonnett
(74) *Attorney, Agent, or Firm* — Malloy & Malloy, P.A.

(57) ABSTRACT

A single use lancet device having a housing, with an open interior and an access opening defined therein, a lancet, with a body and a piercing tip, and disposed in the open interior of the housing so as to move between a cocked orientation and a piercing orientation, a driving assembly structured to move the lancet into the piercing orientation, and a restrictor assembly having a shoulder element and a restrictor panel operatively associated with the lancet and the housing and structured to pass over the restrictor panel upon the lancet moving from its cocked orientation to its piercing orientation, and to abut the restrictor panel upon attempted movement of the lancet back into its cocked orientation after movement into the piercing orientation, thereby preventing the lancet from moving back into the cocked orientation and preventing re-use of a contaminated piercing tip.

6 Claims, 1 Drawing Sheet

U.S. PATENT DOCUMENTS

| | | |
|---|---|---|
| 4,715,374 A | 12/1987 | Maggio |
| 4,735,202 A | 4/1988 | Williams |
| 4,735,203 A | 4/1988 | Ryder et al. |
| 4,752,290 A | 6/1988 | Schramm |
| 4,758,231 A | 7/1988 | Haber et al. |
| 4,794,926 A | 1/1989 | Munsch et al. |
| 4,817,603 A | 4/1989 | Turner et al. |
| 4,823,806 A | 4/1989 | Bajada |
| 4,841,985 A | 6/1989 | Wanamaker |
| 4,863,436 A | 9/1989 | Glick |
| 4,869,249 A | 9/1989 | Crossman et al. |
| 4,889,117 A | 12/1989 | Stevens |
| 4,892,097 A | 1/1990 | Ranalletta et al. |
| 4,895,147 A | 1/1990 | Bodicky et al. |
| 4,897,083 A | 1/1990 | Martell |
| 4,907,600 A | 3/1990 | Spencer |
| 4,908,023 A | 3/1990 | Yuen |
| 4,944,736 A | 7/1990 | Holtz |
| 4,969,883 A | 11/1990 | Gilbert et al. |
| 4,983,178 A | 1/1991 | Schnell |
| 4,990,154 A | 2/1991 | Brown et al. |
| 4,994,045 A | 2/1991 | Ranford |
| 4,994,068 A | 2/1991 | Hufnagle |
| 5,024,660 A | 6/1991 | McNaughton |
| 5,026,388 A | 6/1991 | Ingalz |
| 5,057,079 A | 10/1991 | Tiemann et al. |
| 5,070,885 A | 12/1991 | Bonaldo |
| 5,074,872 A | 12/1991 | Brown et al. |
| 5,086,780 A | 2/1992 | Schmitt |
| 5,088,996 A | 2/1992 | Kopfer et al. |
| 5,116,351 A | 5/1992 | Frassetti |
| 5,125,921 A | 6/1992 | Duschek |
| 5,147,326 A | 9/1992 | Talonn et al. |
| 5,147,375 A | 9/1992 | Sullivan et al. |
| 5,160,326 A | 11/1992 | Talonn et al. |
| 5,181,609 A | 1/1993 | Spielmann et al. |
| 5,188,620 A | 2/1993 | Jepson et al. |
| 5,201,716 A | 4/1993 | Richard |
| 5,207,696 A | 5/1993 | Matwijcow |
| 5,207,699 A | 5/1993 | Coe |
| 5,219,333 A | 6/1993 | Sagstetter et al. |
| 5,222,945 A | 6/1993 | Basnight |
| 5,224,950 A | 7/1993 | Prywes |
| 5,230,707 A | 7/1993 | Laderoute |
| 5,241,969 A | 9/1993 | Carson et al. |
| 5,247,972 A | 9/1993 | Tetreault |
| 5,250,026 A | 10/1993 | Ehrlich et al. |
| 5,250,063 A | 10/1993 | Abidin et al. |
| 5,269,799 A | 12/1993 | Daniel |
| 5,279,581 A | 1/1994 | Firth et al. |
| 5,297,599 A | 3/1994 | Bucheli |
| 5,304,136 A | 4/1994 | Erskine et al. |
| 5,304,192 A | 4/1994 | Crouse |
| 5,304,193 A | 4/1994 | Zhadanov |
| 5,312,347 A | 5/1994 | Osborne et al. |
| 5,312,354 A | 5/1994 | Allen et al. |
| 5,312,365 A | 5/1994 | Firth et al. |
| 5,318,583 A | 6/1994 | Rabenau et al. |
| 5,318,584 A | 6/1994 | Lange et al. |
| 5,330,492 A | 7/1994 | Haugen |
| 5,336,199 A | 8/1994 | Castillo et al. |
| 5,346,480 A | 9/1994 | Hess et al. |
| 5,350,392 A | 9/1994 | Purcell et al. |
| 5,356,406 A | 10/1994 | Schraga |
| 5,356,420 A | 10/1994 | Czernecki et al. |
| 5,361,902 A | 11/1994 | Abidin et al. |
| 5,395,388 A | 3/1995 | Schraga |
| 5,417,662 A | 5/1995 | Hjertman et al. |
| 5,423,847 A | 6/1995 | Strong et al. |
| 5,439,473 A | 8/1995 | Jorgensen |
| 5,454,828 A | 10/1995 | Schraga |
| 5,462,535 A | 10/1995 | Bonnichsen et al. |
| 5,464,418 A | 11/1995 | Schraga |
| 5,468,233 A | 11/1995 | Schraga |
| 5,469,964 A | 11/1995 | Bailey |
| 5,487,748 A | 1/1996 | Marshall et al. |
| 5,496,340 A | 3/1996 | Abidin et al. |
| 5,501,672 A | 3/1996 | Firth et al. |
| 5,514,152 A | 5/1996 | Smith |
| 5,518,004 A | 5/1996 | Schraga |
| 5,527,334 A | 6/1996 | Kanner et al. |
| 5,531,713 A | 7/1996 | Mastronardi et al. |
| D376,203 S | 12/1996 | Schraga |
| 5,584,846 A | 12/1996 | Mawhirt et al. |
| 5,599,323 A | 2/1997 | Bonnichsen et al. |
| 5,628,764 A | 5/1997 | Schraga |
| 5,628,765 A | 5/1997 | Morita |
| 5,643,306 A | 7/1997 | Schraga |
| 5,697,916 A | 12/1997 | Schraga |
| 5,706,942 A | 1/1998 | Vila et al. |
| 5,707,384 A | 1/1998 | Kim |
| 5,709,700 A | 1/1998 | Hirota |
| 5,730,753 A | 3/1998 | Morita |
| 5,735,823 A | 4/1998 | Berger |
| 5,738,665 A | 4/1998 | Caizza et al. |
| 5,741,288 A | 4/1998 | Rife |
| 5,746,761 A | 5/1998 | Turchin |
| 5,755,733 A * | 5/1998 | Morita .......................... 606/182 |
| 5,772,636 A | 6/1998 | Brimhall et al. |
| 5,792,122 A | 8/1998 | Brimhall et al. |
| 5,797,940 A | 8/1998 | Mawhirt et al. |
| 5,797,942 A | 8/1998 | Schraga |
| 5,836,920 A | 11/1998 | Robertson |
| 5,868,771 A | 2/1999 | Herbert et al. |
| 5,871,494 A | 2/1999 | Simons et al. |
| 5,873,856 A | 2/1999 | Hjertman et al. |
| 5,891,103 A | 4/1999 | Burns |
| 5,908,434 A | 6/1999 | Schraga |
| 5,916,230 A | 6/1999 | Brenneman et al. |
| 5,947,934 A | 9/1999 | Hansen et al. |
| 5,951,530 A | 9/1999 | Steengaard et al. |
| 5,951,582 A | 9/1999 | Thorne et al. |
| 5,954,738 A | 9/1999 | LeVaughn et al. |
| 5,968,021 A | 10/1999 | Ejlersen |
| 5,971,966 A | 10/1999 | Lav |
| 5,980,491 A | 11/1999 | Hansen |
| 5,984,906 A | 11/1999 | Bonnichsen et al. |
| 6,015,397 A | 1/2000 | Elson et al. |
| 6,022,366 A | 2/2000 | Schraga |
| 6,050,977 A | 4/2000 | Adams |
| 6,056,765 A | 5/2000 | Bajaj et al. |
| 6,074,372 A | 6/2000 | Hansen |
| 6,077,253 A | 6/2000 | Cosme |
| 6,106,537 A | 8/2000 | Crossman et al. |
| 6,110,149 A | 8/2000 | Klitgaard et al. |
| 6,136,013 A | 10/2000 | Marshall et al. |
| 6,149,608 A | 11/2000 | Marshall et al. |
| 6,156,051 A | 12/2000 | Schraga |
| 6,168,606 B1 | 1/2001 | Levin et al. |
| 6,190,398 B1 | 2/2001 | Schraga |
| 6,213,977 B1 | 4/2001 | Hjertman et al. |
| 6,216,868 B1 | 4/2001 | Rastegar et al. |
| 6,228,100 B1 | 5/2001 | Schraga |
| 6,248,120 B1 | 6/2001 | Wyszogrodzki |
| 6,258,112 B1 * | 7/2001 | Schraga .......................... 606/181 |
| 6,299,626 B1 | 10/2001 | Viranyi |
| 6,302,869 B1 | 10/2001 | Klitgaard |
| 6,322,574 B1 | 11/2001 | Lloyd et al. |
| 6,322,575 B1 | 11/2001 | Schraga |
| 6,346,114 B1 | 2/2002 | Schraga |
| 6,358,265 B1 | 3/2002 | Thorne, Jr. et al. |
| 6,432,120 B1 | 8/2002 | Teo |
| 6,514,270 B1 | 2/2003 | Schraga |
| 6,530,937 B1 | 3/2003 | Schraga |
| 6,719,771 B1 | 4/2004 | Crossman |
| 6,764,496 B2 * | 7/2004 | Schraga .......................... 606/182 |
| 6,852,119 B1 | 2/2005 | Abulhaj et al. |
| 6,887,253 B2 | 5/2005 | Schraga |
| 6,918,918 B1 | 7/2005 | Schraga |
| 6,949,111 B2 | 9/2005 | Schraga |
| 6,958,072 B2 | 10/2005 | Schraga |
| 7,105,006 B2 | 9/2006 | Shraga |
| 7,575,583 B1 | 8/2009 | Schraga |
| 7,621,931 B2 | 11/2009 | Shraga |
| 7,678,126 B2 | 3/2010 | Schraga |
| 2002/0004649 A1 | 1/2002 | Jansen et al. |
| 2004/0102802 A1 | 5/2004 | Marshall |

| | | | |
|---|---|---|---|
| 2004/0147948 A1 | 7/2004 | Schraga | |
| 2005/0070945 A1 | 3/2005 | Schraga | |
| 2005/0245955 A1 | 11/2005 | Schraga | |
| 2006/0058828 A1 | 3/2006 | Shi | |
| 2006/0079920 A1 | 4/2006 | Schraga | |
| 2006/0178686 A1 | 8/2006 | Schraga | |
| 2006/0184189 A1 | 8/2006 | Olson et al. | |
| 2010/0305598 A1 | 12/2010 | Schraga | |

FOREIGN PATENT DOCUMENTS

| | | |
|---|---|---|
| CA | 2 450 711 A1 | 6/2003 |
| CN | 2621601 | 6/2004 |
| CN | 03220517.1 | 6/2004 |
| CN | 02815771.0 | 10/2004 |
| CN | 00817325.7 | 6/2005 |
| CN | 1846612 A | 10/2006 |
| DE | 203 13 528 U1 | 1/2004 |
| EP | 0 115 388 A1 | 8/1984 |
| EP | 0 293 092 A | 11/1988 |
| EP | 0 595 148 A1 | 5/1994 |
| EP | 0 633 004 A1 | 1/1995 |
| EP | 0 668 049 A1 | 8/1995 |
| EP | 0 894 471 A2 | 2/1999 |
| EP | 0 940 121 A2 | 9/1999 |
| EP | 0 958 783 A1 | 11/1999 |
| EP | 1 233 706 | 8/2002 |
| EP | 1 501 428 | 2/2005 |
| FR | 1.126.718 | 11/1956 |
| GB | 2 052 992 A | 2/1981 |
| HK | 1055234 B | 2/2006 |
| JP | 2003-512883 A | 4/2003 |
| JP | 2005-511191 A | 4/2005 |
| JP | 2006-218301 A | 8/2006 |
| WO | WO 91/00215 | 1/1991 |
| WO | WO 95/16400 A1 | 6/1995 |
| WO | WO 98/55034 | 12/1998 |
| WO | WO 00/78203 A2 | 12/2000 |
| WO | WO 00/78214 A1 | 12/2000 |
| WO | WO 01/32086 A1 | 5/2001 |
| WO | WO 03/049624 A1 | 6/2003 |
| WO | WO 03/092512 A1 | 11/2003 |

* cited by examiner

SINGLE USE LANCET ASSEMBLY

CLAIM OF PRIORITY

The present patent application is a Continuation of patent application having Ser. No. 10/894,865 filed on Jul. 20, 2004 and now abandoned, which is a Continuation-In-Part application of U.S. patent application having Ser. No. 09/903,877 which was filed on Jul. 10, 2001 which matured into U.S. Pat. No. 6,764,496 on Jul. 20, 2004, which is a continuation-in-part patent application having Ser. No. 09/432,351 which was filed on Nov. 2, 1999 and which issued as U.S. Pat. No. 6,258,112 on Jul. 10, 2001, both of which are hereby incorporated by reference.

BACKGROUND OF THE INVENTION

1. Field of the Invention

The present invention relates to a single use lancet assembly which is substantially compact, yet effective for piercing a patient's finger or other body part to obtain a blood sample. The single use lancet device is further configured to be substantially safe to transport and to ensure that subsequent uses of a contaminated lancet tip cannot occur.

2. Description of the Related Art

Lancets are commonly utilized instruments which are employed both in hospitals and other medical facilities, as well as by private individuals, such as diabetics, in order to prick or pierce a patient's skin, typically on a finger of a patient, thereby leading to the generation of a blood sample which can be collected for testing. Because of the wide spread use of such lancets, there are a variety of lancet devices which are available for utilization by patients and/or practitioners in a variety of different circumstances.

For example, a typical lancet may merely include a housing with a sharp piercing tip that is pushed into the patient's skin. More commonly, however, lancet devices, which house a piercing tip and/or a lancet, have been developed which effectively encase and fire the lancet into the patient's skin, thereby eliminating the need for the person taking the sample to actually push the lancet tip into the skin.

Within the various types of specialized lancet devices, one variety is typically configured for multiple and/or repeated uses, while another category is particularly configured for single use, after which the entire device is disposed of. Looking in particular to the single use, disposable lancet devices, such devices typically include a housing which contains and directs or drives a piercing tip into the patient's skin, and which is disposed of along with the used lancet. Naturally, so to make such disposable devices cost effective for frequent use, such devices tend to be rather simplistic in nature providing only a sufficient mechanism for firing, and not overly complicating the design so as to minimize that cost.

While existing single use devices are generally effective for achieving the piercing of the skin required for effective operation, such single use, disposable devices typically do not incorporate a large number of safety features to ensure the safe use and disposal of the device. For example, one primary area of safety which must be addressed with all lancet devices pertains to the purposeful and/or inadvertent reuse of a contaminated lancet. Unfortunately, most currently available single use lancet devices are configured such that after a use thereof has been achieved, it is possible for a patient to re-cock the device, thereby allowing for a subsequent, inappropriate use.

As a result, it would be highly beneficial to provide a single use lancet device which is substantially compact and disposable, can be manufactured in a substantially cost effective manner, and which nevertheless is substantially safe to utilize, affirmatively preventing re-use, once contaminated.

SUMMARY OF THE INVENTION

The present invention relates to a single use lancet device configured to pierce a patient's skin and be useable only a single time, thereby preventing reuse of a contaminated lancet piercing tip. In particular, the present single use lancet device includes a housing having an open interior area and an access opening defined therein. The housing is preferably compact and includes a lancet disposed within its open interior.

Looking to the lancet, it is preferably of the type which includes a body and a piercing tip. It is the piercing tip which includes the pointed configuration structured to penetrate or pierce a patient's skin for the drawing of blood. Moreover, the lancet is cooperatively disposed within the open interior of the housing such that the lancet may move between at least a cocked orientation and a piercing orientation wherein the patient's skin is penetrated by the piercing tip.

Also operatively associated with the lancet is a driving assembly. The driving assembly is structured to move or drive the lancet, at least temporarily, into the piercing orientation from the cocked orientation. Preferably, however, the device is configured such that the cocked orientation is generally maintained until affirmatively released by a user. Along these lines, the present single use lancet device also includes an actuation button operatively associated with the lancet. The actuation button is structured to protrude from the housing, at least when the lancet is disposed in the cocked orientation, so as to be effectively actuatable. When the lancet is in the cocked orientation, the actuation assembly maintains the lancet in that cocked orientation, however, when it is actuated, such as by being pushed inward, the lancet is released from the cocked orientation and the driving assembly propels the lancet at least temporarily into its piercing orientation wherein the piercing tip protrudes through the access opening of the housing.

In order to ensure that lancet device can only be used a single time, the present single use lancet device further includes abutment structure cooperatively disposed between the housing and the lancet. The abutment structure is configured to prevent the lancet from moving into the cocked orientation after movement into the piercing orientation. Preferably, the abutment structure includes a shoulder element and a restrictor panel operatively associated with the lancet and the housing. In particular, the shoulder element is structured to pass over the restrictor panel when the lancet moves from its cocked orientation to its piercing orientation. Conversely, however, when a user attempts to move the lancet back into the cocked orientation after it moved into the piercing orientation, the restrictor panel abuts the shoulder element preventing further movement. As a result, movement of the lancet into the cocked orientation is prevented once the lancet has been used a single time, and subsequent uses of a contaminated lancet are prevented.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
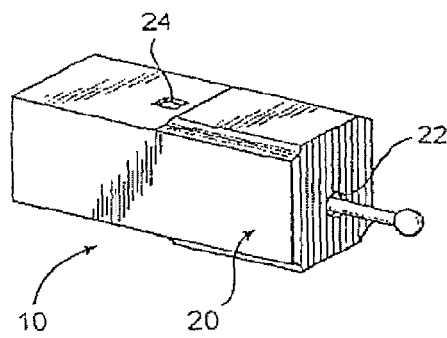
FIG. 1 is a perspective illustration of an embodiment of the single use lancet device of the present invention.

Shown throughout the Figures, the present invention is directed towards a single use lancet device, generally indicated as 10. In particular, the single use lancet device 10 of the present invention includes a housing, generally indicated as 20. The housing 20 is preferably substantially small and compact, and may be made of one or a plurality of segments, preferably of a generally rigid, disposable material, such as plastic. The housing 20 includes an at least partially open interior 28 and at least one access opening 22 defined therein. The open interior 28 of the housing 20 is preferably sized and configured to effectively receive a lancet, generally 30 therein.

Figure 3:
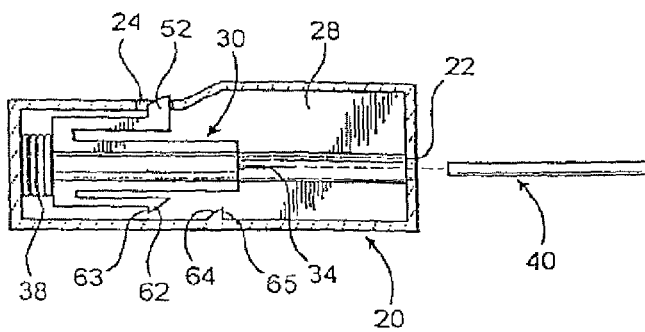
FIG. 3 is a side cross section view of the single use lancet device of the present invention in a cocked orientation.

In particular, the lancet device 10 of the present invention also comprises a lancet 30. The lancet 30 preferably includes a body 32 and a piercing tip 34. The piercing tip 34 is what will be used to pierce a person's skin so as to draw blood to be utilized for a sample and or test procedure. Moreover, the body 32 may be the shaft of the piercing tip 34 and/or an additional structure such as that depicted in the Figures. Regardless, however, the lancet 30 is structured to move within the open interior 28 of a housing 20, preferably at least between a cocked orientation, as depicted in FIG. 3, and a piercing orientation wherein the piercing tip 34 of lancet 30 at least temporarily protrudes through the access opening 22.

Figure 2:
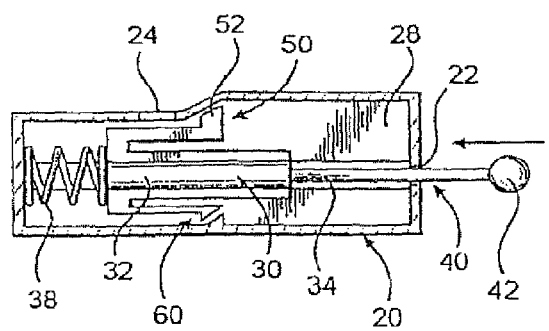
FIG. 2 is a side cross section view of the single use lancet device of the present invention in an unused, initially un-cocked orientation.

Looking in further detail to the illustrated lancet device 10, and the path of movement of the lancet 30 within the housing 20, when the lancet device 10 is initially obtained for use, the lancet 30 is preferably maintained in an un-used, initially un-cocked and pre-fired orientation, as best seen in FIG. 2. In this initially un-cocked and pre-fired orientation a protective cover 40 preferably extends into the open interior 28 of the housing 20 so as to at least partially and removably cover the piercing tip 34 of the lancet 30, thereby maintaining the safety and sterility of the piercing tip 34 when not being used. In this regard, the protective cover 40 may be formed from a variety of preferably rigid materials and is structured to protrude from the housing 20. Furthermore, the protective cover 40 may include an enlarged head 42 configured to facilitate grasping thereof.

Preferably utilizing the protective cover 40, the protective cover 40 is structured to be pushed inwardly into the housing by a user, as depicted by the arrows on FIG. 2, thereby pushing the lancet 30 further into the housing 20. Such pushing of the lancet 30 into the housing 20 results in a positioning of the lancet 30 in its cocked orientation, best illustrated in FIG. 3. Once in the cocked orientation, the protective cover 40 is then structured to be removable from the piercing tip 34, such as by a twisting thereof, thereby leaving the piercing tip 34 completely exposed for use.

The single use lancet of the present invention further includes a driving assembly, generally 38. The driving assembly 38 is particularly configured to move the lancet 30 at least temporarily into its piercing orientation wherein the piercing tip 34 protrudes through the access opening 22 of the housing 20 a desired amount. In particular, if desired, a depth adjustment structure could be positioned at the access opening to control the amount which the piercing tip protrudes from the housing 20. For example, a threaded washer type element could be adjustably secured to the housing 20 in generally surrounding relation to the access opening 22.

Figure 4:
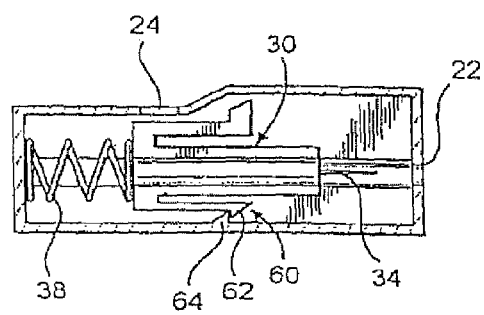
FIG. 4 is a side cross section view of the single use lancet device of the present invention after it has moved into a piercing orientation from the cocked orientation.

Looking further to the driving assembly, preferably the driving movement occurs when the lancet 30 is released from its cocked orientation. In the illustrated embodiment, the driving assembly 38 includes a biasing element operatively disposed between the lancet 30 and the housing 20. Moreover, in the illustrated embodiment a spring is preferably utilized, however, it is recognized that a variety of other driving assemblies can be utilized, including a wedge assembly, a hammer type assembly and/or a resilient material plate, segment or extension, all of which may be configured to move the lancet 30 from the cocked orientation into the piercing orientation. Further, it is preferred that based upon the sizing of the housing 20 and the nature and size of the driving assembly 38, that after the lancet 30 has moved into the piercing orientation wherein the piercing tip 34 protrudes through the access opening 22, the lancet tends to be retracted back into the housing, as best illustrated in FIG. 4. As a result, the used piercing tip 34 is effectively concealed within the housing 20 subsequent to usage, protecting against inadvertent engagement between a person and the used piercing tip 34.

In order to retain, and subsequently effectively release the lancet 30 from its cocked orientation, the single use lancet of the present invention further includes an actuation assembly, generally, 50. Although a variety of different actuation assemblies may be incorporated so as to retain and then release the lancet 30 from its cocked orientation, which in the illustrated embodiment allows the driving assembly to be released from its compressed orientation, the actuation assembly includes an actuation button 52. In the illustrated embodiment, the actuation button 52 is structured to at least temporarily protrude from the housing 20, such as through an actuation aperture 24. Furthermore, the actuation button 52 is preferably secured, either directly or indirectly to the lancet 30, so as to generally restrict movement of the lancet 30 from the cocked orientation when the actuation button 52 protrudes from the housing 20. As a result, the cocked orientation is maintained while the actuation button protrudes from the housing 20. Specifically, in the illustrated embodiment, the actuation button 52 extends from the body 32 of the lancet 30 by a biased segment, and as such, by abutting the housing 20 within the actuation opening 24, movement of the lancet 30 from the cocked orientation is prevented. When, however, the actuation button 52 is actuated, such as by being pushed inwardly, into the housing, it is at least temporarily concealed within the housing 20, removing the abutting engagement and allowing the lancet 30 to freely move within the housing 20, at least temporarily into the piercing orientation. Although the preceding defines the illustrated actuation assembly, it is understood that a variety of alternative actuation assemblies, such as including separate elements to retain and to release the lancet may also be provided, and or including structures which are actually part of the driving assembly and/or remain at least partially exposed and actuatable at all times, may also be provided.

Figure 5:
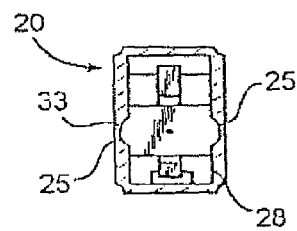
FIG. 5 is a front cross section view of the single use lancet device of the present invention.

Looking in particular to FIG. 5, movement of the lancet 30 through the housing 20 is preferably maintained in a substantially linear path by a guide assembly. In the illustrated embodiment, the guide assembly includes at least one guide ridge 33 protruding from the body 32 of the lancet 30, and at least one corresponding guide track 25 structured to movably receive the guide ridge 33 therein. The guide track 25 preferably extends at least partially along a length of the open interior 28 of the housing 20 so as to maintain the guide ridge 33 effectively therein during a necessary range of motion of the lancet 30. As depicted in FIG. 5, preferably a pair of guide ridges 33 are disposed on opposite sides of the lancet body 32, with a corresponding pair of oppositely disposed guide tracks 25 being defined in the housing. It is of course, however, understood that the guide tracks 25 need not necessarily be directly defined in the housing 20, but may be additional elements secured therein, and conversely the guide track(s) may be defined in or on the lancet body 32, with the guide ridge(s) extending inwardly from the housing 20.

The single use lancet 10 of the present invention further includes a restrictor assembly, generally indicated as 60. The restrictor assembly 60 is structured to substantially prevent the lancet 30 from moving back into the cocked orientation of FIG. 3 after it has moved, even momentarily, into the piercing orientation wherein a patient's skin may be pierced and the piercing tip 34 becomes contaminated. In this regard, the cocked orientation may be defined by the lancet being positioned such that actuation of the actuation assembly causes the driving assembly to urge the lancet into the piercing orientation. In the illustrated embodiment, the restrictor assembly 60 is structured such that when the lancet 30 is disposed in the initially un-cocked orientation, as best seen in FIG. 2, movement of the lancet 30 back into the cocked orientation can effectively result despite the restrictor assembly 60. After, however, the lancet 30 has moved into its piercing orientation wherein the piercing tip 34 has protruded through the access opening 22 of the housing 20, the restrictor assembly is configured such that the lancet 30 can no longer be pushed back into the cocked orientation. As a result, a patient can neither accidentally nor purposefully reuse the single use lancet 10 of the present invention after it has been fired.

In the illustrated embodiment, the restrictor assembly 60 includes an abutment structure cooperatively disposed between the housing 20 and the lancet 30. The abutment structure is configured to physically prevent movement of the lancet back into the cocked orientation. Preferably, the abutment structure comprises a shoulder element 62 and a restrictor panel 64 configured to freely pass one another when the lancet 30 moves from the cocked orientation to the piercing orientation, but also configured to abut one another upon attempted movement of the lancet 30 back into the cocked orientation after it has moved into the piercing orientation. Looking to FIG. 4, the illustrated shoulder element 62 includes an at least partially slopped and preferably biased configuration, such as an elongate biased finger that at least partially retracts inward towards the body 32 of the lancet 30 so as to facilitate passage thereof past the restrictor panel 64. In this regard, preferably mating slopped surfaces are provided on the shoulder element 62 and the restrictor panel 64, thereby facilitating the sliding passages past one another, and indeed, promoting an at least partial retraction of the shoulder element 62 to further facilitate this passage past one another, upon movement of the lancet 30 in a first direction towards the access opening 22 of the housing 20. The shoulder element 62 is also, however, structured to generally expand after it has passed the restrictor panel 64, such as back into its normal unretracted and/or un-compressed orientation, such that it will abut the restrictor panel 64 upon attempted movement of the lancet 30 in a second direction opposite the access opening 22 of the housing 20.

Although an opposite configuration could be just as effectively utilized, in the illustrated embodiment, the biased finger 62 of the shoulder element extends from the lancet 30, preferably generally toward the piercing tip 34 of the lancet 30, while the restrictor panel 64 protrudes from the housing 20, extending into the open interior 28 of the housing 20. Along these lines, the restrictor panel 64 includes a protruding element preferably with the aforementioned slopped configuration which downwardly slopes away from the piercing tip 34 of the lancet 30 facilitating the aforementioned sliding passage past the shoulder element 62.

So as to provide generally secure movement restriction through effective abutment, both the shoulder element 62 and the restrictor panel 64 each preferably include abutment surfaces 63 and 65, respectably. The abutment surfaces 63 and 65 are structured to generally engage and abut one another, as best illustrated in FIG. 4, thereby preventing movement of the lancet 30 back into the cocked orientation. In the illustrated embodiment, the abutment surfaces 63, 65 are generally flat, although it is recognized that interlocking fingers or wedges, and/or other types of engaging structures that prevent relative movement in at least one direction could also be effectively utilized.

Figure 6:
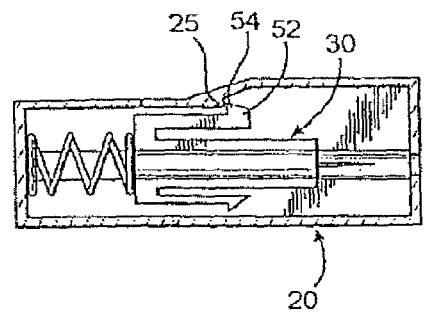
FIG. 6 is a side cross section view of another embodiment of the single use lancet device of the present invention after the lancet has moved from the cocked orientation through the piercing orientation.

Addressing further the restrictor assembly of the present invention, it is understood that a variety of different restrictor assemblies may be effectively utilized which prevent movement of a lancet 30 back into a cocked orientation after the lancet 30 has moved sufficiently forward and/or has moved into the piercing orientation. As such, the embodiment illustrated in FIGS. 2 through 5 is merely a single illustration of a preferred contemplated embodiment, and other alternative embodiments are also considered within the scope of the restrictor assembly of the present invention. By way of example, and looking specifically to FIG. 6, the actuation button 52 may comprise part of the restrictor assembly. In such an embodiment, a restrictor panel 25 is defined in the housing 20, and the actuation button 52 as part of the biased finger of the shoulder element, includes an abutment surface 54 which engages a confronting surface of the restrictor panel 25. In such an embodiment, the initially un-cocked orientation provides for the actuation button 52 to be initially disposed rearward of the restrictor panel 25 so as to permit movement of the lancet 30 at least initially into the cocked orientation. Moreover, in this embodiment, the previous embodiment, and/or any other alternative embodiment, if desired, the protective cover 40 may be equipped with an interior shield segment or other configuration which extends into the housing and maintains the biased finger of the shoulder element 62, or another component of the restrictor assembly, in a generally compressed and/or retracted orientation until the protective cover 40 is removed. As a result, in such an embodiment, so long as the protective cover 40 is maintained on the piercing tip 34, the lancet 30 is always able to return the cocked orientation. Preferably, however, re-positioning of the protective cover onto the piercing tip in such a manner as to be able to "reset" the lancet 30, allowing its movement once again into the cocked orientation, will be prevented.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A single use lancet device comprising:
a housing;
a lancet;
said lancet including a piercing tip;
said lancet at least partially disposed in said housing and structured to move at least between a cocked orientation and a piercing orientation;
a biasing element structured to move said lancet at least temporarily into said piercing orientation;
an actuator structured to be actuated by a user so as to result in said biasing element moving said lancet at least temporarily into said piercing orientation;
a restrictor assembly, at least part of said restrictor assembly being independent of said biasing element, and said lancet, and when engaged structured to prevent said lancet from being moved back into said cocked orientation after movement of said lancet at least temporarily into said piercing orientation as a result of an implement pushing merely said lancet;
said restrictor assembly comprising an abutment structure including a shoulder element and a restrictor panel;
said restrictor panel and said shoulder element structured to pass one another upon said lancet moving from said cocked orientation to said piercing orientation and to abut one another upon attempted movement of said lancet into said cocked orientation after movement into said piercing orientation;
said shoulder element structured to retract out of a normal unretracted orientation during passage past said restrictor panel and to expand back to said normal unretracted orientation after passage past said restrictor panel, so as to facilitate passage of said restrictor panel and said shoulder element past one another in a first direction corresponding to movement of said lancet from said cocked orientation to said piercing orientation and to block movement of said restrictor panel in a second direction, generally opposite to the first direction, subsequent to said passage past one another in the first direction; and
said shoulder element comprising a biased finger extending from and attached directly to said lancet and said restrictor panel comprising a protruding element protruding from and directly attached to a side wall of said housing.

2. A single use lancet as recited in claim 1 wherein said biasing element comprises a spring.

3. A single use lancet as recited in claim 1 wherein said actuator comprises a button structured to protrude from said housing when said lancet is disposed in said cocked orientation.

4. A single use lancet as recited in claim 1 wherein said protruding element includes a sloped configuration which downwardly slopes away from said piercing tip of said lancet so as to facilitate passage thereof past said biased finger upon said lancet moving in the first direction towards an access opening.

5. A single use lancet as recited in claim 1 further comprising a protective cover structured to at least partially and removably cover said piercing tip of said lancet at least prior to movement of said lancet into said cocked orientation.

6. A single use lancet device comprising:
a housing;
a lancet;
said lancet including a piercing tip;
said lancet at least partially disposed in said housing and structured to move at least between a cocked orientation and a piercing orientation;
a biasing element structured to move said lancet at least temporarily into said piercing orientation;
an actuator structured to be actuated by a user so as to result in said biasing element moving said lancet at least temporarily into said piercing orientation;
a restrictor assembly, at least a portion of said restrictor assembly being independent of said biasing element and structured to engage said lancet independently of user interaction with said actuator after said lancet has moved into said piercing orientation, and thereby prevent said lancet from being moved back into said cocked orientation after movement of said lancet at least temporarily into said piercing orientation merely as a result of an implement pushing said lancet;
said restrictor assembly including a shoulder element and a restrictor panel, said restrictor panel and said shoulder element structured to pass one another upon said lancet moving from said cocked orientation to said piercing orientation, and to abut one another upon attempted movement of said lancet into said cocked orientation after movement into said piercing orientation;
said shoulder element including a biased finger extending from and attached directly to said lancet;
said restrictor panel including a protruding element protruding from and directly attached to a side wall of said housing; and
said shoulder element structured to retract out of a normal unretracted orientation during passage past said restrictor panel and to expand back to said normal unretracted orientation after passage past said restrictor panel.

* * * * *